United States Patent [19]

Murakmi et al.

[11] Patent Number: 5,527,843

[45] Date of Patent: *Jun. 18, 1996

[54] BLOOD SEPARATING COMPOSITION

[75] Inventors: Kazunori Murakmi, Kusatsu; Hiroshi Sudo, Shiga-ken; Kazumi Sakurai; Hitoshi Tanaka, both of Otu, all of Japan

[73] Assignee: Nissho Corporation, Osaka, Japan

[*] Notice: The term of this patent shall not extend beyond the expiration date of Pat. No. 5,304,605.

[21] Appl. No.: 277,372

[22] Filed: Jul. 20, 1994

Related U.S. Application Data

[63] Continuation of Ser. No. 951,811, Sep. 28, 1992, abandoned.

[30] Foreign Application Priority Data

Oct. 16, 1991 [JP] Japan ................................. 3-298487

[51] Int. Cl.$^6$ .................................................. C08K 5/20
[52] U.S. Cl. .......................... 524/227; 524/262; 524/413; 524/425; 524/588; 524/516; 252/60; 252/315.01
[58] Field of Search .................................. 524/262, 413, 524/425, 588, 227; 210/516; 252/60, 315.01

[56] References Cited

U.S. PATENT DOCUMENTS

| | | | |
|---|---|---|---|
| 4,021,340 | 5/1977 | Zine, Jr. ................................... | 210/83 |
| 4,101,422 | 7/1978 | Lamont et al. .......................... | 210/789 |
| 4,148,764 | 4/1979 | Lamont et al. .......................... | 106/253 |
| 4,172,803 | 10/1979 | Ichikawa et al. ........................ | 252/60 |
| 4,230,584 | 10/1980 | Ichikawa et al. ........................ | 210/516 |
| 4,828,720 | 5/1989 | Kuroda et al. ........................... | 210/782 |
| 4,994,393 | 2/1991 | Pradhan et al. .......................... | 436/8 |
| 5,304,605 | 4/1994 | Murakami et al. ..................... | 524/227 |
| 5,354,838 | 10/1994 | Murakami et al. ..................... | 528/272 |

FOREIGN PATENT DOCUMENTS

| | | |
|---|---|---|
| 0035575 | 9/1981 | European Pat. Off. . |
| 0375566 | 6/1990 | European Pat. Off. . |
| 2743882 | 3/1978 | Germany . |
| 1-313757 | 12/1989 | Japan . |
| WO91/08246 | 6/1991 | WIPO . |

*Primary Examiner*—Paul R. Michl
*Assistant Examiner*—John J. Guarriello
*Attorney, Agent, or Firm*—Armstrong, Westerman, Hattori, McLeland & Naughton

[57] ABSTRACT

A blood separating composition for use in blood collection tubes, the composition having an absolute viscosity of 100,000–320,000 cP at 25° C. at a shear rate of 1 sec$^{-1}$ when the blood separating composition turns into its dynamic state from its stationary state, with a reduced viscosity of 50,000 cP or more at a shear rate of 10 sec$^{-1}$ in the dynamic state. The absolute viscosity of said composition is 100,000–300,000 cP at the shear rate of 1 sec$^{-1}$ when returning to the stationary state. Such a viscosity renders stable and less flowable and blood separating composition during storage, allowing it to form a stable partition barrier in each collection tube when centrifuged to separate the blood phases one from another, with the blood cells above the barrier being prevented from remaining within the serum. The blood separating composition does not release any harmful oily substance or the like.

2 Claims, No Drawings

BLOOD SEPARATING COMPOSITION

This application is a continuation of application Ser. No. 07/951,811 filed Sep. 28, 1992, now abandoned.

BACKGROUND OF THE INVENTION

1. Field of the Invention

The present invention relates to a blood separating composition for use in the centrifugal separation of the blood components such as serum and plasma, wherein the difference in the specific gravity between the blood components are utilized.

2. Prior Art

There are known various types of the blood separating compositions which are used to separate the blood components from one another. The main ingredient in the compositions is a gel material, for example a silicone oil, a chlorinated polybutene or an acrylic polymer. A thixotropic agent such as silica or clay is usually added to the main ingredient of the blood separating composition, which is to be previously set in place on the bottom of a blood collection tube so as to provide a blood testing receptacle. A blood sample will be taken in the blood testing receptacle, and be maintained in this state for a given period of hours before being centrifuged. The centrifugal force causes the blood separating composition to be fluidized, and it will gradually ascend off the bottom because its specific gravity is intermediate the specific gravity of the serum or plasma and that of the blood cells. Thus, a barrier is formed between the layer of serum or plasma and the layer of blood cells, to thereby separate the former layer from the latter.

The prior art blood separating composition containing the thixotropic agent has been problematic about its thixotropic property, as will be described below.

As well known in the art, thixotropy is such a phenomenon that a material which shows in its stationary state a higher viscosity will become less viscous and substantially flowable under the influence of an external force or stress applied thereto, provided that the force exceed a certain strength. Upon removal of the external force, this material however will recover gradually and slowly its high viscosity. In other words, a certain length of time is necessary for such a material to change from its less viscous state back into its highly viscous state, after the external force is removed.

The certain strength of the external force for changing the material from its stationary state to its dynamic one is called a yield stress. Likewise, another yield stress will be observed also when the material returns from its dynamic state to its stationary state.

The cause of this mechanism is considered to be a weak intermolecular force such as the hydrogen bonds which may take place between the molecules of the gel material as main ingredient, between the molecules of the added thixotropic agent, and/or between the former molecules and the latter ones.

Such a thixotropic property will play an important or decisive role in the blood separation by the blood separating composition, as will be described below.

The viscosity and the yield stress when the blood separating composition changes from its stationary state to its dynamic state gives influence on its ascendability and/or flowability. In detail, the composition resting on the bottom of a vacuum blood collection tube will move towards an upper end thereof closed with a rubber plug, in a manner depending on the viscosity and yield stress. Further, the blood separating composition will ascend to the upper end at a timing also depending on the viscosity of said composition in its dynamic state. On the other hand, the viscosity and another yield stress of the blood separating composition returning from its dynamic state to its stationary state will affect the self-standing property or strength, and/or the reversibility of the barrier after the centrifugal separation process.

In more detail, the following problems will occur when the centrifugal separation is carried out after a proper period of time for a blood collection tube which contains on its bottom the blood separating composition and a given volume of a blood to be tested.

If the blood separating composition will not become flowable to ascend off the bottom of the blood collection tube in spite of the centrifugal force applied, then any barrier will not be formed between the layer of serum or plasma and the layer of blood cells, thus causing a direct contact of the former with the latter. If the barrier which is formed by the flowable and ascending blood separating composition is not self-standing but peels off the wall of said blood collection tube, then there will occur not only the direct contact of the two layers, but also some blood cells will remain above the barrier in the phase of the serum or plasma. If the blood separating composition on the bottom of the vacuum blood collection tube will incidentally move towards the upper end thereof closed with a rubber plug, then a significant amount of the composition will remain the phase of serum or plasma, or will stick to the rubber plug, thereby causing the contamination of said phase or the difficulty in obtaining a pure sample of serum or plasma.

Almost all of the prior art blood separating compositions are prepared taking no account of such a thixotropy, and consequently, none of them is free from the abovementioned problems.

SUMMARY OF THE INVENTION

The present inventors have conducted a series of researches and studies to resolve the above problems, and developed a novel and practically useful type of the blood separating composition which is so thixotropic that in use an excellent ascendability is ensured to form a stable barrier when centrifuged.

According to the present invention, there is provided a blood separating composition containing a proper thixotropic agent, wherein the absolute viscosity of the composition is 100,000–320,000 cP at a shear rate of 1 $sec^{-1}$ at 25° C. when the blood separating composition changes from its stationary state to its dynamic one, with a reduced viscosity of 50,000 cP or more at a raised shear rate of 10 $sec^{-1}$ in the dynamic state, and the absolute viscosity of said composition is 100,000–300,000 cP at the shear rate of 1 $sec^{-1}$ when changing reversely to its stationary state.

The blood separating composition of the present invention desirably has a yield stress of 30–400 $dyn/cm^2$ for the change from its stationary state to its dynamic one at 25° C., and another yield stress of 20–200 $dyn/cm^2$ for the reverse change from its dynamic state to its stationary one.

DETAILED DESCRIPTION OF THE INVENTION

The more preferable absolute viscosity of the blood separating composition is: 130,000–200,000 cP at a shear rate of 1 $sec^{-1}$ when turning into the dynamic state; 70,000 cP or more at a higher shear rate of 10 sec$^{-1}$ in the dynamic state; and 110,000–190,000 cP at the shear rate of 1 sec$^{-1}$ when returning to the stationary state. The unit "sec$^{-1}$" (that is, 1/sec ) is employed to indicate the shear rate ( i.e., velocity / distance ) observed in a sample when its absolute viscosity is measured using for example the E-type rotary viscometer which comprises a conical rotor. With "N" representing the rotational speed in RPM of the rotor, and with φ representing the slope angle in radian ( i.e., rad ) of its conical surface, the shear rate is given by: 2 πN / 60×1 / φ. If the conical surface angle is inclined at an angle of 3° =π/60 rad ( its diameter being 28 mm ), then the rotor will produce a shear rate of 2N sec$^{-1}$. Thus, the shear rate of 1 sec$^{-1}$ will be obtained by setting the rotational speed at 0.5 RPM.

Thixotropic materials such as the blood separating composition generally change in their viscosity depending upon their shear rate. Therefore, the value "cP" or "P" of their viscosity should be given for particular shear rates. In a measurement system in which the absolute viscosity of the material is measured while raising its shear rate for example from 1 sec$^{-1}$ to 10 sec$^{-1}$ and subsequently lowering it from 10 sec$^{-1}$ to 1 sec$^{-1}$, some characteristic or indicator values may be defined as follows. A first one of such characteristic values will be the absolute viscosity at the shear rate of 1 sec$^{-1}$ when the material becomes dynamic. A second characteristic value will be the absolute viscosity observed at the shear rate of 10 sec$^{-1}$ while the material is in the dynamic state, and a third characteristic value will be the absolute viscosity observed at the shear rate of 1 sec$^{-1}$ when said material becomes stationary.

The yield stress for the blood separating composition of the present invention may more desirably be 100–200 dyn/cm$^2$ to cause the change from the stationary state to the dynamic one at 25 ° C., and 30–150 dyn/cm$^2$ to cause the reverse change from the dynamic state to the stationary one.

The yield stress ( in dyn/cm$^2$ or in N/m$^2$ ) is the critical stress observed when the blood separating composition turns into its dynamic state or into its stationary state.

Typically, Casson's yield stress "s" is determined using Casson's fluidity equation: $s^{1/2}=s_c^{1/2}+(\mu_c D)^{1/2}$ wherein "s" is shear stress, "D" denotes the shear rate, and $\mu_c$ denotes Casson's viscosity. This equation indicates that there is a proportional relationship between the function "$s^{1/2}$" and the variable "$D^{1/2}$". Values of these function and variable, i.e., the square roots of "s" and "D", are taken along the axis of ordinates and the axis of abscissas, respectively. The values "$s^{1/2}$" are plotted for the increasing variable "$D^{1/2}$" and a straight line is drawn through the dots, while said values "$s^{1/2}$" also being plotted for the decreasing variable "$D^{1/2}$" to produce another straight line. The axis of ordinates is cut by the two straight lines at such points that can be squared to give the Casson's yield stress for the increasing shear rate "s" and that for the decreasing shear rate, respectively. The former stress is defined as the yield stress for the material turning into the dynamic state, and the latter is defined as the other yield stress for said material turning into the stationary state.

The blood separating composition, whose viscosity and yield stress respectively exceed 320,000 cP and 400 dyn/cm$^2$ for the shear rate 1 sec$^{-1}$ at 25 ° C. when turning into the dynamic state, has a poor ascendability in the centrifugal separation process. However, the viscosity and yield stress respectively lower than 100,000 cP and 30 dyn/cm$^2$ will render excessively flowable the gel, i.e., the blood separating composition. In the latter case, this composition is likely to undesirably and incidentally move towards a rubber plug closing the mouth of a vacuum blood collection tube, in which said composition is initially placed to rest on the bottom. Such an incident will cause the contamination of the serum or plasma with and/or the sticking of the blood separating composition to the rubber plug.

If the viscosity is below 50,000 cP at the higher shear rate of 10 sec$^{-1}$ in the dynamic state, then the timing at which the blood separating composition will ascend during the centrifugal separation process becomes much earlier than desired. Thus, the composition ascending towards the mouth will scarcely adhere to the wall of the blood collection tube, and the barrier which said composition forms in the centrifugal process cannot be stable to a satisfactory degree. On the other hand, the blood separating composition, whose viscosity and yield stress are respectively below 100,000 cP and 20 dyn/cm$^2$ for the shear rate 1 sec$^{-1}$ when returning to the stationary state, will take a longer time for the barrier to be kept in place after the the centrifugal process. However, the viscosity and yield stress respectively exceeding 300,000 cP and 200 dyn/cm$^2$ at 1 sec$^{-1}$ of the composition returning to the stationary state will adversely affect its ascendability during the centrifugal process, because the viscosity and yield stress for the change into the dynamic state cannot fall within the abovementioned range.

Nowadays, the blood collection tubes made of plastics are used widely in addition to those which are made of a glass. The blood separating composition must have the thixotropic property which matches the kind of material of the tube in which the composition is accommodated.

The viscosity as one factor of the thixotropic property of the composition adapted for use in the glass tubes is desirably: 140,000–200,000 cP at 1 sec$^{-1}$ when turning into the dynamic state; 70,000 cP or more at 10 sec$^{-1}$ in the dynamic state; and 100,000–190,000 cP at 1 sec$^{-1}$ when returning to the stationary state. The yield stress as the other factor of this composition is: 100–350 dyn/cm$^2$ for the change to the dynamic state; and 30–150 dyn/cm$^2$ for the reverse change to the stationary state.

It is desirable that the viscosity as the one factor of the thixotropic property of the composition adapted for use in the plastics tubes is: 120,000–190,000 cP at 1 sec$^{-1}$ when turning into the dynamic state; 60,000 cP or more at 10 sec$^{-1}$ in the dynamic state; and 100,000–170,000 cP at 1 sec$^{-1}$ when returning to the stationary state. The yield stress as the other factor of this composition is: 30–280 dyn/cm$^2$ for the change to the dynamic state; and 20–100 dyn/cm$^2$ for the reverse change to the stationary state.

The gel material as the main ingredient of the blood separating composition in the invention is not delimited to a particular compound, but may be any one of the usually employed compounds including a silicone oil, a chlorinated polybutene, and a copolymer of diester of α-olefin and maleic acid. Those compounds preferably have a specific gravity of 1.035–1.055 at 25 ° C., with a viscosity of 30,000–150,000 cP at 1 sec$^{-1}$ when turning into the dynamic state. Since the gel material as the main ingredient is almost not thixotropic, its character can be defined by the viscosity at 1 sec$^{-1}$ when it becomes dynamic or flowable.

If the specific gravity is below 1.035 and the viscosity at 1 sec$^{-1}$ for changing from the stationary state to the dynamic one is below 30,000 cP, then the blood separating composition produced will be highly mobile and less stable in position under the gravitational force or the like, thus failing to ensure a durability in storage. If the blood separating composition on the bottom of the vacuum blood collection tube will incidentally move towards the upper end thereof closed with a rubber plug, then a significant amount of the composition will remain in the phase of serum or plasma, or will stick to the rubber plug, thereby causing the contamination of said phase or the difficulty in obtaining a pure sample of serum or plasma.

If contrarily the specific gravity is above 1.055 and the viscosity at 1 sec$^{-1}$ for turning into the dynamic state is above 150,000 cP, then the composition produced will be of a poor ascendability. Further, such a high viscosity will render difficult the handling and inputting of said composition into the blood collection tubes.

One of the preferred gel materials is a copolymer of sebacic acid with 2,2-dimethyl-1,3-propanediol and 1,2-propanediol. Particularly, the molar ratio 1.02–1.07 of these diols to sebacic acid is desirable, because the aforementioned good property is ensured. This gel material withstands well the radiation sterilization such as the gamma ray irradiation, and is not caused thereby to make any change in its physical and/or chemical properties.

The thixotropic agent employed in the blood separating composition of the invention is also not delimited to a particular compound, but may be any one of an amide of fatty acid, silica, clay and the like. A small amount of the fatty acid amide added to the copolymer as the gel material will suffice to give it the gel property requisite to the blood separating composition. The number of carbon atoms per molecule of the employed fatty acid amide or a mixture of fatty acid amides may be 10–25, or more desirably 16–18.

In case of employing the fatty acid amide(s) as the thixotropic agent, 0.5–7 parts by weight or more desirably 1–4 parts by weight thereof may be added to the gel material.

Such a content of the fatty acid amide(s) will realize an optimal flowability of the blood separating composition, whereby the shape stability, the durability in storage, the ascendability and the strength of barrier are all improved.

In an easy process of producing the blood separating composition, the gel material, for example the copolymer of sebacic acid with 2,2-dimethyl-1,3-propanediol and 1,2-propanediol, will be heated at first to a temperature of about 60°–80 °C. A given amount of the thixotropic agent, for example the fatty acid amide(s) is then added to the heated gel material so as to form a mixture. A shearing force will continuously be applied to the mixture which is being heated until its components melt and become homogeneously blended.

The blood separating composition provided by the present invention must be of a specific gravity intermediate those of the serum phase and the clot phase, or intermediate the plasma phase and the clot phase. Therefore, the specific gravity of the composition has to fall within a range of 1,035 to 1.060. In a case wherein a given amount of the blood separating composition is placed on the bottom of a blood collection/separation tube, the greater the difference in specific gravity between the clot or blood cell phase and the composition, the better the asendability thereof would be when subjected to the centrifugal separation process. If however the blood separating composition is of a specific gravity below 1,035, a fraction of such a lighter blood separating composition will undesirably remain in the phase of serum or plasma which has been centrifugally separated.

The blood separating composition may further contain an inorganic material, for example titanium dioxide, calcium carbonate or the like so that the specific gravity and/or the viscosity are adjusted to their desirable levels.

THE PREFERRED EMBODIMENTS

Next, the present invention will be described in more detail referring to the embodiments, to which the scope of the invention is not delimited.

According to the invention, the desirable viscosity of a blood separating composition is defined, including the thixotropy thereof. With regard to the thixotropy, it is important to carry out the measurement of absolute viscosity for varied shear rates, by using for example an E-type viscometer. The parameters such as the consistency, the needle penetration or the dynamic viscosity of the composition are not adequate herein. The E-type viscometer which is a rotary viscometer (whose cone angle is 3° and diameter is 28 mm) made by Tokyo Keiki Co., Ltd. was used in the preferred embodiments to measure the viscosity at 25° C.

The specific gravity of the blood separating composition was measured herein by the copper sulfate method, in which several copper sulfate solutions of different specific gravity are used. In this method, a drop of the sample is put in each solution at 25° C. in order to find one solution in which the drop neither sinks to the bottom nor floats on the surface of said solution.

The yield stress of the blood separating composition was measured in a manner such that the logarithm values of the shear rate are graduated along the axis of abscissas on a graph, and the logarithm values of the shear stress (graduated along the axis of ordinates) are plotted to give a straight line. The value at a point where the straight line intersects the axis of ordinates is taken to be squared to give the yield stress, i.e., Casson's yield stress.

The viscosity of a copolymer of sebacic acid with 2,2-dimethyl-1,3-propanediol and 1,2-propanediol was measured at 25° C. by detecting the viscosity at a shear rate of 1 sec$^{-1}$ when turning into the dynamic state. The specific gravity of this copolymer was also measured at 25° C.

EXAMPLE NO. 1

100 parts by weight of the copolymer (viscosity; 150,000 cP, specific gravity; 1,042) of sebacic acid with 2,2-dimethyl-1,3-propanediol and 1,2-propanediol, 2 parts by weight of stearamide and 2 parts by weight of "fine silica" (in this Example, "Aerosil 130" made by Nippon Aerosil Co., Ltd.) were blended with one another to give Example No. 1 of the blood separating composition.

EXAMPLE NO. 2

100 parts by weight of the copolymer (viscosity; 150,000 cP, specific gravity; 1.042) of sebacic acid with 2,2-dimethyl-1,3-propanediol and 1,2-propanediol, 1 part by weight of stearamide, and 2 parts by weight of "fine silica" (in this Example, "Aerosil 200" from Nippon Aerosil Co., Ltd.) were blended with one another to give Example No. 2 of the blood separating composition.

EXAMPLE NO. 3

100 parts by weight of the copolymer (viscosity; 68,000 cP, specific gravity; 1.042) of sebacic acid with 2,2-dimethyl-1,3-propanediol and 1,2-propanediol, 1 part by weight of stearamide, and 2 parts by weight of "fine silica" ("Aerosil 130" from Nippon Aerosil Co., Ltd.) were blended with one another to give Example No. 3 of the blood separating composition.

EXAMPLE NO. 4

100 parts by weight of the copolymer ( viscosity; 68,000 cP, specific gravity; 1.042 ) of sebacic acid with 2,2-dimethyl-1,3-propanediol and 1,2-propanediol was blended with 4 parts by weight of stearamide to give Example No. 4 of the blood separating composition.

EXAMPLE NO. 5

100 parts by weight of the copolymer ( viscosity; 68,000 cP, specific gravity; 1,042 ) of sebacic acid with 2,2-dimethyl-1,3-propanediol and 1,2-propanediol was blended with 2 parts by weight of stearamide to give Example No. 5 of the blood separating composition.

EXAMPLE NO. 6

100 parts by weight of the copolymer ( viscosity; 35,000 cP, specific gravity; 1.042 ) of sebacic acid with 2,2-dimethyl-1,3-propanediol and 1,2-propanediol was blended with 2 parts by weight of stearamide to give Example No. 6 of the blood separating composition.

EXAMPLE NO. 7

100 parts by weight of the copolymer ( viscosity; 68,000 cP, specific gravity; 1.042 ) of sebacic acid with 2,2-dimethyl-1,3-propanediol and 1,2-propanediol, 1 part by weight of stearamide, and 2 parts by weight of "fine silica" ( "Aerosil 200" from Nippon Aerosil Co., Ltd. ) were blended with one another to give Example No. 7 of the blood separating composition.

Reference No. 1

100 parts by weight of the copolymer ( viscosity; 150,000 cP, specific gravity; 1.042 ) of sebacic acid with 2,2-dimethyl-1,3-propanediol and 1,2-propanediol was blended with 4 parts by weight of stearamide to provide the Reference No. 1 of the blood separating composition.

Reference No. 2

100 parts by weight of the copolymer ( viscosity; 150,000 cP, specific gravity; 1.02 ) of sebacic acid with 2,2-dimethyl-1,3-propanediol and 1,2-propanediol, 2 part by weight of stearamide, and 2 parts by weight of "fine silica" ( "Aerosil 200" from Nippon Aerosil Co., Ltd. ) were blended with one another to give the Reference No. 2 of the blood separating composition.

Reference No. 3

100 parts by weight of the copolymer ( viscosity; 35,000 cP, specific gravity; 1.042 ) of sebacic acid with 2,2-dimethyl-1,3-propanediol and 1,2-propanediol was blended with 1 part by weight of stearamide, to provide the Reference No. 3 of the blood separating composition.

The absolute viscosity as well as the yield stress were measured, and the stability during storage as well as the capability of dividing blood phases were evaluated under the conditions given below.

1. Measurement of Absolute Viscosity and Yield Stress

VISCOSITY

Samples of the blood separating compositions were placed in the viscometer and were kept still for 5 minutes before the successive measurements of viscosity carried out as follows:

Measurement-1: at the shear rate of 1 $sec^{-1}$ for 5 minutes;

Measurement-2: at the shear rate of 2 $sec^{-1}$ for 5 minutes;

Measurement-3: at the shear rate of 5 $sec^{-1}$ for 5 minutes;

Measurement-4: at the shear rate of 10 $sec^{-1}$ for 5 minutes;

Measurement-5: at the shear rate of 5 $sec^{-1}$ for 5 minutes;

Measurement-6: at the shear rate of 2 $sec^{-1}$ for 5 minutes; and

Measurement-7: at the shear rate of 1 $sec^{-1}$ for 5 minutes.

The value obtained by Measurement-1 corresponds to the absolute viscosity at 1 $sec^{-1}$ when turning into the dynamic state from the stationary state, with the value by Measurement-4 thereby giving the absolute viscosity at 10 $sec^{-1}$ in the dynamic state, and the further value by the Measurement-7 thus corresponding to the absolute viscosity at 1 $sec^{-1}$ when returning to the stationary state.

Taking into account the relaxation of stress which might occur in the sample during each Measurement at the different shear rates, the average of initial three data in each Measurement was taken as the absolute viscosity at the respective shear rates.

YIELD STRESS

Measurement-8: The yield stress of the blood separating compositions was obtained by the method mentioned above. In detail, the logarithm values of the shear rate were graduated along the axis of abscissas on a graph, and the logarithm values of the shear stress for Measurement -1 to Measurement-4 ( detected by the viscometer for the respective shear rates and graduated along the axis of ordinates ) were plotted to give a straight line. The value at a point where the straight line intersected the axis of ordinates was taken to be squared to give the yield stress observed when the compositions turned into their dynamic state.

Measurement-9: The further or second yield stress of the blood separating compositions was obtained likewise by the same method as mentioned above. With the logarithm values of the shear rate being graduated along the axis of abscissas on the graph, the logarithm values of the shear stress for Measurement-4 to Measurement-7 ( detected by the viscometer for the respective shear rates ) were also plotted to give a further straight line. The value at a point where the further straight line intersected the axis of ordinates was taken to be squared to similarly give the further yield stress observed when the compositions returned to their stationary state.

The results obtained by these Measurements for the Examples 1 to 7 and the References 1 to 3 are shown in Tables and 2.

TABLE 1

| Samples | Example 1 | Example 2 | Example 3 | Example 4 | Example 5 |
|---|---|---|---|---|---|
| (Viscosity in cP) | | | | | |
| Meas.-1 | 322,000 | 281,500 | 201,500 | 186,000 | 148,500 |
| Meas.-2 | 269,167 | 250,167 | 167,833 | 140,000 | 114,833 |
| Meas.-3 | >200,000 | >200,000 | 139,267 | 108,200 | 87,600 |
| Meas.-4 | >100,000 | >100,000 | >100,000 | 93,466 | 75,500 |

TABLE 1-continued

| Samples | Example 1 | Example 2 | Example 3 | Example 4 | Example 5 |
| --- | --- | --- | --- | --- | --- |
| Meas.-5 | >200,000 | >200,000 | 139,267 | 103,400 | 80,266 |
| Meas.-6 | 269,167 | 250,167 | 156,833 | 124,500 | 90,833 |
| Meas.-7 | 297,333 | 265,000 | 179,000 | 152,000 | 104,333 |
| (Yield stress, dyn/cm$^2$) | | | | | |
| Meas.-8 | 276 | 108 | 190 | 325 | 264 |
| Meas.-9 | 82 | 25 | 81 | 149 | 48 |

Notes:
"Meas." = measurement

TABLE 2

| Samples | Example 6 | Example 7 | Refer. 1 | Refer. 2 | Refer. 3 |
| --- | --- | --- | --- | --- | --- |
| (Viscosity in cP) | | | | | |
| Meas.-1 | 138,500 | 130,000 | 414,500 | 370,500 | 92,500 |
| Meas.-2 | 105,000 | 115,167 | 332,500 | 297,500 | 89,333 |
| Meas.-3 | 86,666 | 101,467 | >200,000 | >200,000 | 86,133 |
| Meas.-4 | 79,833 | 94,066 | >100,000 | >100,000 | 83,400 |
| Meas.-5 | 83,000 | 98,733 | >200,000 | >200,000 | 83,533 |
| Meas.-6 | 90,000 | 107,833 | 332,500 | 297,500 | 83,666 |
| Meas.-7 | 98,666 | 118,667 | 385,000 | 329,000 | 84,000 |
| (Yield stress, dyn/cm$^2$) | | | | | |
| Meas.-8 | 148 | 65 | 526 | 466 | 6 |
| Meas.-9 | 21 | 31 | 224 | 92 | 20 |

Notes:
"Meas." = measurement
"Refer." = Reference

2. Stability during Storage

The stability of during storage of the blood separating composition was evaluated herein by means of the "flow distance".

Blood collection/separation tubes made of glass and those made of polyethylene terephthalate, having an inner diameter of 13.6 mm, were used. A small amount of a blood separating composition of "Example" of "Reference" weighing

TABLE 3

| | Flow distance (mm) | | | |
| --- | --- | --- | --- | --- |
| Material of tube | Glass | | PET (*) | |
| Temperature and period of storage | 40° C. for 336 hr. | 60° C. for 72 hr. | 40° C. for 336 hr. | 60° C. for 72 hr. |
| Examples | | | | |
| No. 1 | 0 | 3 | 0 | 3 |
| No. 2 | 1 | 10 | 1 | 9 |
| No. 3 | 1 | 3 | 0 | 2 |
| No. 4 | 1 | 1 | 1 | 1 |
| No. 5 | 1 | 1 | 1 | 1 |
| No. 6 | 3 | 3 | 3 | 3 |
| No. 7 | 4 | 8 | 3 | 8 |
| References | | | | |
| No. 1 | 0 | 1 | 0 | 1 |
| No. 2 | 0 | 3 | 0 | 3 |
| No. 3 | 19 | 25 | 19 | 25 |

Notes:
"PET" = polyethylene terephthalate 1.5 grams was put into each tube, and after being kept still and horizontal at 25° C. for 24 hours, an "initial" position of said composition was marked. Subsequently, each tube containing the blood separating composition was kept still and horizontal at 40° C. for 336 hours, or at 60° C. for 72 hours, so as to detect a "final" position of said composition. The data of "flow distance" which is the distance between the initial position and the final position are given on Table 3.

As will be seen from the data in Table 3, the blood separating composition of the present invention was more stable even if stored for a long time, and less flowable within the tubes when transported, than the blood separating compositions represented by the Reference samples.

3. Capability of Dividing Blood Phases

Similarly, blood collection/separation tubes made of glass and or polyethylene terephthalate, having an inner diameter of 13.6 mm, were used. A small amount of a blood separating composition of an "Example" or "Reference" weighing 1.7 grams was put into each tube, and kept therein at 25° C. for 24 hours after storage at 40° C. for 336 hours.

9 ml of human whole blood was put into each tube, and after complete coagulation thereof, the tubes were centrifuged at 1,300 G for 10 minutes ( "G" being the gravitational acceleration ).

Performance or capability of the blood separating composition was evaluated as to the following items, according to the standards given below.

The term "ascendability" used herein indicates the extent to which the blood separating composition can rise in the centrifuged collection tube previously filled with a given amount of human blood. A rating symbol "+++" ('excellent') was allotted to the separating composition which completely rose within the blood collection tube, while another symbol "++" ('good') means a small amount of said composition remained on the tube bottom. A further rating symbol "+" ('poor') represents a significant amount of the blood separating composition which was left on the bottom, whereas a still further symbol "±" ('worst') denotes a quite unsatisfactory rising of the separation means which fully remained on said tube bottom.

Further, the "stability of partition barrier" between the serum and the clot was judged based on the state of said barrier sticking to the tube wall, when 24 hours had passed after the centrifugal separation process. Similarly to the "rising" property, the rating symbols "+++" (excellent), "++" (good), "+" (poor) and "±" (worst) respectively indicate: the perfectly sticking barrier; partially loosened barrier; significantly loosened barrier; and thoroughly loosened barrier.

The "released amount of oily substance" from the separation means was inspected by observation of the serum surface.

"Reddishness" of the serum was checked to determine whether or not any significant number of blood cells had been left in the serum, and also to determine whether or not hemolysis had occurred.

Test results are given in Tables 4 and 5 respectively for the glass tubes and for the polyethylene terephthalate tubes.

TABLE 4

| | Ascendability | Stability of partition | Oily substance released | Reddishness of serum |
| --- | --- | --- | --- | --- |
| Examples | | | | |
| No. 1 | + | +++ | Null | No(*) |
| No. 2 | ++ | +++ | Null | No |

TABLE 4-continued

| | Ascend-ability | Stability of partition | Oily substance released | Reddishness of serum |
|---|---|---|---|---|
| No. 3 | +++ | +++ | Null | No |
| No. 4 | +++ | +++ | Null | No |
| No. 5 | +++ | +++ | Null | No |
| No. 6 | +++ | +++ | Null | No |
| No. 7 | +++ | ++ | Null | No |
| References | | | | |
| No. 1 | ± | ± | Null | No |
| No. 2 | ± | ± | Null | No |
| No. 3 | +++ | ± | Present | A little |

Notes:
"No" = no mixing of blood cells in serum
+++ = excellent
++ = good
+ = poor
± = worst

TABLE 5

| | Ascend-ability | Stability of partition | Oily substance released | Reddishness of serum |
|---|---|---|---|---|
| Examples | | | | |
| No. 1 | + | +++ | Null | No |
| No. 2 | ++ | +++ | Null | No |
| No. 3 | ++ | +++ | Null | No |
| No. 4 | ++ | +++ | Null | No |
| No. 5 | +++ | +++ | Null | No |
| No. 6 | +++ | +++ | Null | No |
| No. 7 | +++ | +++ | Null | No |
| References | | | | |
| No. 1 | ± | ± | Null | No |
| No. 2 | ± | ± | Null | No |
| No. 3 | +++ | ± | Present | A little |

Notes:
"No" = no mixing of blood cells in serum
+++ = excellent
++ = good
+ = poor
± = worst It will be seen from the data of Tables 4 and 5 that in the blood phase-separating operation using the blood separating compositions provided in the invention, not only ascendability but also stability of the partition barrier are excellent and satisfactory. Besides, there is observed neither any amount of oily substance released nor any extent of hemolysis or any number of blood cells remaining in the serum.

It will now be apparent from the above description that the blood separating composition provided by the invention is advantageous in its high separating capability and its good stability which are not affected by a long storage period or the like. It does neither move adversely within the collection tubes during transportation thereof, nor change in its rising property in the centrifugal process, thus maintaining its high capability of separating blood phases. Further, the separation means will not release any oily substance which will give undesirable influence on the operation of testing apparatuses.

What is claimed is:

1. In a blood separating composition comprising a gel material as a main ingredient and a thixotropic agent added to and blended with the gel material; the improvement wherein the absolute viscosity of the composition is 100,000–190,000 cP at 25° C. at a shear rate of 1 $sec^{-1}$ when the blood separating composition turns into its dynamic state from its stationary state, with a reduced viscosity of 50,000 cP or more at a raised shear rate of 10 $sec^{-1}$ in the dynamic state, and the absolute viscosity of said composition is 100,000–190,000 cP at the shear rate of 1 $sec^{-1}$ when returning to the stationary state.

2. A blood separation composition as defined in claim 1, wherein the blood separating composition has a yield stress of 30–400 $dyn/cm^2$ for the change from its stationary state to its dynamic one at 25° C. and another yield stress of 20–200 $dyn/cm^2$ for the reverse change from its dynamic state to its stationary one.

* * * * *